United States Patent
Sawin et al.

[11] Patent Number: 5,916,546
[45] Date of Patent: *Jun. 29, 1999

[54] DEODORANT COSMETIC STICK COMPOSITIONS

[75] Inventors: Philip Andrew Sawin, Cincinnati, Ohio; John Paul Luebbe, Lawrenceburg, Ind.; Gerald Joseph Quinlivan, Maineville, Ohio

[73] Assignee: Procter & Gamble Company, Cincinnati, Ohio

[*] Notice: This patent issued on a continued prosecution application filed under 37 CFR 1.53(d), and is subject to the twenty year patent term provisions of 35 U.S.C. 154(a)(2).

[21] Appl. No.: 08/841,184

[22] Filed: Apr. 29, 1997

Related U.S. Application Data

[63] Continuation of application No. 08/551,093, Oct. 31, 1995, abandoned.

[51] Int. Cl.⁶ .............................. A61K 7/32; A61K 7/34; A61K 7/36; A61K 7/38
[52] U.S. Cl. ................ 424/65; 424/66; 424/67; 424/68; 424/DIG. 5
[58] Field of Search ................ 424/65, 66, 67, 424/68, DIG. 5

[56] References Cited

U.S. PATENT DOCUMENTS

| | | | |
|---|---|---|---|
| 5,531,986 | 7/1996 | Shevade et al. | 424/68 |
| 5,547,661 | 8/1996 | Sun et al. | 424/66 |
| 5,756,082 | 5/1998 | Cashin et al. | 424/78.03 |
| 5,833,965 | 11/1998 | Sun et al. | 424/66 |
| 5,874,069 | 2/1999 | Mendolia et al. | 424/65 |

*Primary Examiner*—Robert H. Harrison
*Attorney, Agent, or Firm*—William J. Winter; Tara M. Rosnell

[57] ABSTRACT

A cosmetic stick deodorant composition comprising: a. from about 0.5% to about 10.0% of the cosmetic stick deodorant composition of an astringent metal salt active; b. a stable, anhydrous base component comprising: i. from about 5% to about 40% of the cosmetic stick deodorant composition of a solidifying agent selected from the group consisting of the high melting point waxes; and low melting point wax fatty alcohols, fatty acid esters and fatty acid amides, having fatty chains of from about 8 to about 22 carbon atoms, and mixtures thereof; ii. from about 20% to about 70% of the cosmetic stick deodorant composition of a volatile emollients; iii. from about 10% to about 50% of the cosmetic stick deodorant composition of non-volatile emollients; and c. from about 0.05% to about 10% of the cosmetic stick deodorant composition of a solubilizing agent having a hydrophile-lipophile balance (HLB) value of greater than about 10.

14 Claims, No Drawings

DEODORANT COSMETIC STICK COMPOSITIONS

This is a continuation of application Ser. No. 08/551,093, filed on Oct. 31, 1995 abandoned.

FIELD OF THE INVENTION

The present invention relates to deodorant cosmetic stick compositions containing high levels of emollients and a surfactant. The compositions herein have improved deodorant efficacy, reduced skin irritation and minimized negative component interactions for improved stability. They also possess "wet" cosmetic attributes generally acceptable to deodorant solid users as opposed to "dry" cosmetic attributes more accepted by antiperspirant solid users.

BACKGROUND OF THE INVENTION

Human body malodors are generally believed to be caused in part by by-products of microbial interaction with sweat gland secretions. Aside from cleansing, one way to control such odors is by the use of deodorant or antiperspirant products, particularly in the underarm area of the body.

Deodorant and antiperspirant products may be in any of several forms including, for example, creams, liquids, aerosol liquids solid sticks. Many consumers prefer solid stick-type products. Due to the particular types of ingredients employed in deodorants versus antiperspirants, deodorant sticks are typically of the gel-type, whereas antiperspirant sticks are typically of the wax-type.

Gel stick deodorant compositions have several advantages over other types of stick formulations. For example solid gel sticks glide more smoothly over the skin when applied than wax-type sticks. Furthermore gel sticks tend to leave less visible residue on the skin than wax-type sticks.

Solid deodorant gel stick products generally consist of a safe and effective level of an antimicrobial active ingredient which is incorporated into a solid stick base comprising a solidifying agent, a liquid matrix material to carry the active and non-volatile silicone and/or hydrocarbon emollients to deliver the desired cosmetic feel.

The solidifying agents most often used in the solid base component of gel stick deodorants include fatty acid soaps, particularly sodium stearate, and/or dibenzylidine monosorbitol acetals (hereinafter DBS). The following exemplary patents relate to gel stick compositions utilizing soap solidifying agents: U.S. Pat. Nos. 3,255,082, Barton, issued Jun. 7, 1966; 4,137,306, Rubino, issued Jan. 30, 1979; 4,944,937, McCall, issued Jul. 31, 1990. The following exemplary patents relate to gel stick compositions utilizing DBS solidifying agents: U.S. Pat. Nos. 4,154,816, Roehl et al, issued May 15, 1979; 4,518,582, Schamper et al, issued May 21, 1985; 4,719,102, Randhawa et al, issued Jan. 12, 1988; 4,722,835, Schamper et al, issued Feb. 2, 1988; 4,725,430, Schamper et al, issued Feb. 16, 1988; 4,781,917, Luebbe et al, issued Nov. 1, 1988; 4,816,261, Luebbe et al, issued Mar. 28, 1989; 4,822,602, Sabetelli, issued Apr. 18, 1989; and 5,106,999, Gardlik et al, issued Apr. 21, 1992.

The liquid matrix materials of the solid base component of soap-type and DBS-based gel stick deodorants typically include lower molecular weight alcohols (such as ethanol and isopropanol), and glycols (such as propylene glycol, diethylene glycol, dipropylene glycol, butylene glycol and various higher polyethylene and polypropylene glycols). The following exemplary patent relates gel stick compositions utilizing alcohols and glycols: U.S. Pat. No. 4,137,306, Rubino, issued Jan. 30, 1979. Low molecular weight alcohols and glycols, however, tend to contribute to undesirable performance characteristics such as skin irritation and undesirable stick shrinkage and containment problems due to high volatility.

Silicone and hydrocarbon emollients are used in typical cosmetic stick deodorants. One type of preferred nonvolatile silicone emollient for deodorant sticks is dimethicone. Hydrocarbon emollients typically used in gel stick deodorants include fatty acid and fatty alcohol esters and water insoluble ethers, such as those disclosed in U.S. Pat. No. 4,202,876, Shelton, issued May 13, 1980.

Deodorant compositions typically contain an antimicrobial active ingredient at levels of from about 0.1% to about 10% by weight. Examples of such antimicrobial active ingredients typically included in deodorant compositions include the primary oleamine salt of piroctone (known commercially as Octopirox®), certain metal salts of piroctone acid (such as aluminum, sodium, potassium, zirconium, calcium and zinc metal salts), triclosan, zinc phenolsulfonate, certain heavy metal salts of 1-hydroxy pyridinethione (such as zinc pyrithione, magnesium pyrithione, and aluminum pyrithione) and bacteriostatic quaternary ammonium compounds (such as cetyl-trimethyl ammonium bromide, cetyl pyridinium chloride, benzethonium chloride, and sodium N-lauryl-sarcosine).

Certain astringent metal salts, particularly aluminum and zirconium astringent salts and complexes and some zinc salts, typically used in antiperspirant compositions at levels above about 10% by weight have also been shown to provide deodorancy benefits when employed at levels below about 10% without the antiperspirancy effects. See Plechner, *Antiperspirants and Deodorants*, Cosmetics, Science and Technology—Volume 2, Balsam and Sagarin, 374–411, 1972.

Although shown to provide excellent deodorancy characteristics, astringent metal salts have not generally been used in deodorant solid gel stick products primarily due to incompatibility between the soap-type gellants and polyvalent salts (cations bearing greater than +1 charge). Without being limited by theory, it is believed that the metal salt active interacts with the carboxylate functional group on the fatty acid soap resulting in reduced deodorancy efficacy and loss of integrity of the solid itself, resulting in significant softening of the solid stick product.

The aluminum salt actives are also incompatible with DBS and DBS-type solidifying agents, as they tends to degrade the acetal portion of the DBS gellant resulting in reduced efficacy of the actives, poor gel formation, and lower gel stability over time, as well as processing difficulties at the temperatures and holding times typically encountered during manufacturing of the deodorant compositions.

It would be desirable, in view of the excellent deodorancy characteristics of metal salt actives, to incorporate them into cosmetic stick deodorant compositions which provide a stable product with the wet, smooth cosmetic feel and low visible residue typical of deodorant gel sticks. It would also be desirable, in view of the skin-irritation characteristics of low-molecular weight alcohols and glycols to omit or strictly limit the amount of these materials contained in the composition.

The present inventors have found that such cosmetic stick deodorant compositions with astringent metal salt actives, can be produced by incorporating wax solidifying agents in combination with high levels of volatile and non-volatile emollients. The inventors have also found that the efficacy of the astringent metal salt actives can be even further improved by the addition of a surfactant with a high hydrophile-lipophile balance value.

It is therefore an objective of the present invention to provide a deodorant cosmetic stick composition, in which astringent metal salts are used as the deodorant active in a stable, anhydrous base component which exhibits a wet, smooth cosmetic feel and low visible residue. It is a further object of this invention to provide deodorant cosmetic stick compositions which are not irritating to the skin due to low molecular weight alcohols and glycols.

SUMMARY OF THE INVENTION

The present invention relates to a cosmetic stick deodorant composition comprising:
a. from about 0.5% to about 10.0% of the cosmetic stick deodorant composition of an astringent metal salt active;
b. a stable, anhydrous base component comprising:
   i. from about 5% to about 40% by weight of the cosmetic stick deodorant composition of a solidifying agent;
   ii. from about 20% to about 70% by weight of the solid cosmetic stick deodorant composition of volatile emollients;
   iii. from about 10% to about 50% of the solid cosmetic stick deodorant composition of non-volatile silicone and/or hydrocarbon emollients; and
c. from about 0.05% to about 10% of the solid cosmetic stick deodorant composition of a surfactant material having a hydrophile-lipophile balance (HLB) value of greater than about 10.

All percentages and ratios used herein are by weight unless otherwise indicated.

DETAILED DESCRIPTION OF THE INVENTION

Cosmetic stick deodorant compositions of the present invention include the ingredients discussed below. Although the term "stick" as utilized herein includes semi-solid forms, preferably having a viscosity of at least about 1,000,000 centipoise at 25° C., solid forms, preferably having an average penetration value within a given production batch from about 3 to about 25 mm over a period of 5 seconds as measured utilizing American Society for Testing Materials (ASTM) Method D-5, with a penetration cone (Model H1312; sold by Humbolt Manufacturing Company) weighing 2.0 g (making the total mass 50 g and a Sommer & Runge Model PNR10 Penetrometer) are preferred.

A. Astringent Metal Salt Active

The cosmetic stick deodorant compositions of the present invention contain an astringent metal salt active. It has been found that astringent metal salt actives deliver improved deodorancy performance compared to the antimicrobial actives typically employed in deodorant gel sticks. The actives are used at levels ranging from about 0.5% to about 10%, preferably from about 2% to about 9%, more preferably from about 3% to about 7%, and most preferably from about 4% to about 5% of the deodorant cosmetic stick composition. As used herein, the term "metal salt" can include any astringent aluminum or zirconium salt or complex known for use in deodorant or antiperspirant compositions. The metal salt active material is typically incorporated into the deodorant compositions in particulate form.

Any deodorant active consisting of a poly-valent metal salt can be employed herein. Poly-valent metal salts useful as astringent deodorant salts or as components of astringent complexes include aluminum halides, aluminum hydroxyhalides, zirconyl oxyhalides, zirconyl hydroxy-halides, zinc compounds such as zinc phenylsulfonate, zinc glycinate and zinc pyrithione, and mixtures of these materials.

Aluminum salts can include aluminum chloride and the aluminum hydroxyhalides having the general formula $Al_2(OH)_xQ_y \cdot XH_2O$ where Q is chlorine, bromine or iodine; where x is from about 2 to about 5, and x+y=about 6, and x and y do not need to be integers; and where X is from about 1 to about 6. Aluminum salts of this type can be prepared in the manner described more fully in U.S. Pat. No. 3,887,692 issued to Gilman on Jun. 3, 1975, and U.S. Pat. No. 3,904,741 issued to Jones and Rubino on Sep. 9, 1975, both herein included by reference.

Zirconium compounds can include the zirconium oxy salts and zirconium hydroxy salts. These compounds may be represented by the following general empirical formula:

$$ZrO(OH)_{2-nz}B_z$$

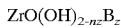

wherein z may vary from about 0.9 to about 2 and need not be an integer, n is the valence of B, 2-nz is greater than or equal to 0, and B may be selected from the group consisting of halides, nitrate, sulfamate, sulfate, and mixtures thereof. Although only zirconium compounds are exemplified in this specification, it will be understood that other Group IVB metal compounds, including hafnium, can be used in the present invention.

As with the basic aluminum compounds, it will be understood that the above formula is greatly simplified and is intended to represent and include compounds having coordinated and/or bound water in various quantities, as well as polymers, mixtures and complexes of the above. As will be seen from the above formula, the zirconium hydroxy salts actually represent a range of compounds having various amounts of the hydroxy group, varying from about 1.1 to only slightly greater than zero groups per molecule.

Several types of complexes utilizing the above identified metal salts are known in the art. For example, U.S. Pat. No. 3,792,068 issued to Luedders et al. on Feb. 12, 1974, herein incorporated by reference, discloses complexes of aluminum, zirconium and amino acids, such as glycine. Complexes such as those disclosed in the above-referenced Luedders et al. patent and other similar complexes are commonly known as ZAG. ZAG complexes are chemically analyzable for the presence of aluminum, zirconium and chlorine. ZAG complexes useful herein are identified by the specification of both the molar ratio of aluminum to zirconium (hereinafter "Al:Zr" ratio) and the molar ratio of total metal to chlorine (hereinafter "Metal:Cl" ratio). ZAG complexes useful herein have an Al:Zr ratio of from about 1.67 to about 12.5 and a Metal:Cl ratio of from about 0.73 to about 1.93.

Preferred ZAG complexes are formed by:
(A) co-dissolving in water:
(1) one part $Al_2(OH)_{6-m}Q_m$, wherein Q is an anion selected from the group consisting of chloride, bromide and iodide, and m is a number from about 0.8 to about 2.0;
(2) x parts $ZrO(OH)_{2-a}Q_a \cdot nH_2O$, where Q is chloride, bromide or iodide; where a is from about 1 to about 2; where n is from about 1 to about 8; and where x has a value of from about 0.16 to about 1.2;
(3) p parts neutral amino acid selected from the group consisting of glycine, dl-tryptophane, dl-b- phenylalanine, dl-valine, dl-methionine and b-alanine, and where p has a value of from about 0.06 to about 0.53;

(B) co-drying the resultant mixture to a friable solid; and (C) reducing the resultant dried inorganic-organic antiperspirant complex to particulate form.

A preferred aluminum compound for preparation of such ZAG-type complexes is aluminum chlorohydroxide of the empirical formula $Al_2(OH)_5Cl.2H_2O$. Preferred zirconium compounds for preparation of such ZAG-type complexes are zirconyl hydroxychloride having the empirical formula $ZrO(OH)Cl.3H_2O$ and the zirconyl hydroxyhalides of the empirical formula $ZrO(OH)_{2-a}Cl_2.nH_2O$ wherein a is from about 1.5 to about 1.87, and n is from about 1 to about 7. The preferred amino acid for preparing such ZAG-type complexes is glycine of the formula $CH_2(NH_2)COOH$. Salts of such amino acids can also be employed in the metal salt complexes. See U.S. Pat. No. 4,017,599 issued to Rubino on Apr. 12, 1977, herein incorporated by reference.

A wide variety of other types of metal salts are also known in the art. For example, U.S. Pat. No. 3,903,258 issued to Siegal on Sep. 2, 1975, incorporated by reference herein, discloses a zirconium aluminum complex prepared by reacting zirconyl chloride with aluminum hydroxide and aluminum chlorohydroxide. U.S. Pat. No. 3,979,510 issued to Rubino on Sep. 7, 1976, incorporated by reference herein, discloses a deodorant complex formed from certain aluminum compounds, certain zirconium compounds, and certain complex aluminum buffers. U.S. Pat. No. 3,981,896 issued to Pauling on Sep. 21, 1976, incorporated by reference herein, discloses a deodorant complex prepared from an aluminum polyol compound, a zirconium compound and an organic buffer. U.S. Pat. No. 3,970,748 issued to Mecca on Jul. 20, 1976, incorporated by reference herein, discloses an aluminum chlorohydroxy glycinate complex of the approximate general formula $[Al_2(OH)_4Cl][H_2CNH_2COOH]$.

Of all the above types of metal salts, preferred compounds include the 5/6 basic aluminum chlorohydroxide salts of the empirical formula $Al_2(OH)_5Cl.2H_2O$; mixtures of $AlCl_3.6H_2O$ and $Al_2(OH)_5Cl. 2H_2O$ with aluminum chloride to aluminum chlorohydroxide weight ratios of up to about 0.5; ZAG-type complexes (aluminum zirconium trichorohydrex glycinate complex) wherein the zirconium salt is $ZrO(OH)Cl.3H_2O$, the aluminum salt is $Al_2(OH)_5Cl.2H_2O$ or the aforementioned mixtures of $AlCl_3.6H_2O$ and $Al_2(OH)_5 Cl.2H_2O$ wherein the total metal to chloride molar ratio in the complex is less than about 1.25 and the Al:Zr molar ratio is about 3.3, and the amino acid is glycine; and ZAG-type complexes wherein the zirconium salt is $ZrO(OH)_{2-a}Cl_a.nH_2O$ wherein a is from about 1.5 to about 1.87 and n is from about 1 to about 7, the aluminum salt is $Al_2(OH)_5Cl.2H_2O$, and the amino acid is glycine.

B. Base Component

The cosmetic stick deodorant compositions of the present invention contain a stable anhydrous solid base component which forms the body of the cosmetic stick deodorant and provides the vehicle for applying the astringent metal salt active to the skin. The base component of the cosmetic stick deodorant compositions of the present invention comprise the ingredients discussed below.

1. Solidifying Agent

The cosmetic stick deodorants of the present invention contain one or more materials, herein singly or collectively referred to as a "solidifying agent", that are effective to solidify the liquid materials of the composition. As is appreciated by those skilled in the art, the selection of the particular solidifying agent for use in the cosmetic stick product will depend upon the particular type of cosmetic stick desired, i.e., the desired rheology, the liquid ingredients and other ingredients used in the composition.

The cosmetic stick deodorant compositions of the present invention contain from about 5% to about 40%, preferably about 10% to about 35%, more preferably from about 15% to about 30% by weight of the solidifying agent. Such solidifying agents useful herein are the high melting point waxes, having a melting point of from about 65° C. to about 102° C., such as beeswax, castor wax, spermaceti wax, carnauba wax, bayberry wax, candelilla wax, montan wax, ozokerite wax, ceresin wax, paraffin wax, synthetic waxes such as Fisher-Tropsch waxes, microcrystalline wax and mixtures thereof. Castor wax, ceresin wax, ozokerite wax, white beeswax, synthetic waxes, and mixtures thereof, are among the preferred high melting point waxes useful herein. Compositions containing waxes among those useful herein are disclosed in U.S. Pat. No. 4,049,792, Elsnau, issued Sep. 20, 1977, incorporated by reference herein.

Also useful as the solidifying agent of the cosmetic stick deodorants of the present invention are the low melting point waxes, having a melting point of from about 37° C. to about 75° C. Such materials include fatty alcohols, fatty acid esters and fatty acid amides, having fatty chains of from about 8 to about 22 carbon atoms, and mixtures thereof. Preferred low melting point wax-like materials useful herein, include cetyl alcohol, palmitic alcohol, stearyl alcohol, behenyl alcohol, sucrose esters of tallow fatty acids, mono and di-fatty acid ester of polyethylene glycol, and mixtures thereof. Stearyl alcohol, cetyl alcohol, behenyl alcohol and mixtures thereof, are particularly preferred. Fatty alcohols and other wax-like materials useful in this invention are also disclosed in the following U.S. Patents, U.S. Pat. No. 4,151,272, Geary, et al., issued Apr. 24, 1979; U.S. Pat. No. 4,229,432, Geria, issued Oct. 21, 1980; and U.S. Pat. No. 4,280,994, Turney, issued Jul. 28, 1981, all incorporated by reference herein. The preferred wax materials useful as solidifying agents in the cosmetic stick deodorant of the present invention are described in U.S. Pat. No. 4,126,679, Davy, et al., issued Nov. 21, 1978, incorporated by reference herein.

2. Volatile and Non-volatile Emollients

The emollients of the present cosmetic stick deodorant compositions of the present invention are typically selected, so when mixed they provide desired aesthetic benefits, such as emolliency, low tack, smooth glide-on application and minimized visible residue, without significant interference with the effectiveness of the metal salt deodorant active component. The emollients, liquid at room temperature, also carry the aluminum salt active in the product and, in processing, solubilize the solidifying agent when heated. It is important that the emollients be of types, and used at levels, sufficient to solubilize the solidifying agent when heated, to permit substantially uniform mixing of the astringent metal salt active into the heated solution at the mixing temperature, and form a stick of desired consistency when cooled to ambient temperature. The emollients must be compatible with the solidifying agent so that their mixture is homogeneous and does not phase separate during manufacturing and so that the finished product and does not phase separate at ambient conditions over the normal shelf-life, which may be upwards of one year. Lastly, the emollients should be safe for application to human skin. Emollient materials can be selected from two classes; volatile emollients and non-volatile emollients.

A. Volatile Emollients

The term "volatile" as used herein refers to materials which exhibit a vapor pressure of more than about 0.2 mm Hg at 25° C. at one atmosphere and/or to materials which have a boiling point at one atmosphere of less than about 300° C. Volatile emollients particularly useful in the present invention are selected from the group consisting of silicone oils, hydrocarbons, and mixtures thereof. Volatile emollients are used in the cosmetic stick deodorant compositions of the present invention at levels from about 20% to about 70%; preferably, from about 30% to about 60%; more preferably from about 40% to about 60%. Such volatile oils are disclosed, for example, in Cosmetics, Science, and Technology, Vol. 1, 27–104 edited by Balsam and Sagarin, 1972, herein incorporated by reference. The volatile hydrocarbon emollients useful in the present invention may be either saturated or unsaturated, have an aliphatic character and be straight or branched chained or contain alicyclic or aromatic rings. Examples of preferred non-polar, volatile hydrocarbon oils include isodecane (such as Permethyl-99A® which is available from Presperse Inc.) and the $C_7$–$C_8$ through $C_{12}$–$C_{15}$ isoparaffins (such as the Isopar® Series available from Exxon Chemicals).

Volatile silicone oils are highly preferred as an emollient in deodorant compositions of the present invention since they endow the stick composition with highly desirable cosmetic characteristics. Volatile liquid silicone oils are disclosed in U.S. Pat. No. 4,781,917 issued to Luebbe et al. on Nov. 1, 1988, (herein incorporated by reference). Additionally, a description of various volatile silicones materials is found in Todd et al., "Volatile Silicone Fluids for Cosmetics", Cosmetics and Toiletries, 91:27–32 (1976), herein incorporated by reference. Particularly preferred volatile silicone oils are selected from the group consisting of cyclic volatile silicones corresponding to the formula:

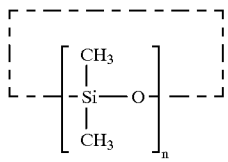

wherein n is from about 3 to about 7; and linear volatile silicones corresponding to the formula:

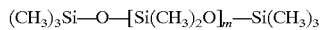

wherein m is from about 1 to about 7. Linear volatile silicones generally have a viscosity of less than about 5 centistokes at 25° C., whereas the cyclic silicones have viscosities of less than about 10 centistokes at 25° C. Highly preferred examples of volatile silicone oils include cyclomethicones of varying viscosities, e.g., Dow Corning 200®, Dow Corning 244®, Dow Corning 245®, Dow Corning 344®, and Dow Corning 345®, (commercially available from Dow Corning Corp.); SF-1204 and SF-1202 Silicone Fluids® (commercially available from G.E. Silicones), GE 7207® and GE 7158® (commercially available from General Electric Co.); and SWS-03314® (commercially available from SWS Silicones Corp.).

B. Non-volatile Emollients

The term "non-volatile" as used herein refers to materials which exhibit a vapor pressure of no more than about 0.2 mm Hg at 25° C. at one atmosphere and/or to materials which have a boiling point at one atmosphere of at least about 300° C. Typical non-volatile emollients are disclosed, for example, in Cosmetics, Science, and Technology, Vol. 1, 27–104 edited by Balsam and Sagarin, 1972; U.S. Pat. No. 4,202,879 issued to Shelton on May 13, 1980; and U.S. Pat. No. 4,816,261 issued to Luebbe et al. on Mar. 28, 1989, all of which are incorporated by reference herein. The non-volatile emollients for use in the deodorant compositions of the present invention can be selected from silicone oils, hydrocarbon oils, and intermediate polarity co-solvent emollients or mixtures thereof. Non-volatile emollients are used in the deodorant compositions of the present invention at levels from about 10% to about 50%; preferably, from about 10% to about 35%; more preferably from about 15% to about 25%.

Non-volatile silicone oils useful in the deodorant compositions of the present invention are essentially non-volatile polysiloxanes. The polysiloxanes useful in the present invention are selected from the group consisting of polyalkylsiloxanes, polyarylsiloxanes, polyalkylarylsiloxanes, poly-ethersiloxane copolymers, and mixtures thereof. Examples of these include polydimethyl siloxanes having viscosities of from about 5 to about 100,000 centistokes at 25° C. Among the preferred polyalkylsiloxane emollients useful in the deodorant compositions of the present invention are the polydimethyl siloxanes having viscosities from about 2 to about 400 centistokes at 25° C. Such polyalkylsiloxanes include the Viscasil® series (sold by General Electric Company) and the Dow Corning 200® series (sold by Dow Corning Corp.). Polyalkylarylsiloxanes include polymethylphenyl siloxanes having viscosities of from about 15 to about 65 centistokes at 25° C. These are available, for example, as SF 1075® methyl-phenyl fluid (sold by General Electric Company) and 556 Cosmetic Grade Fluid® (sold by Dow Corning Corp.). Useful polyethersiloxane copolymers include, for example, a polyoxyalkylene ether copolymer having a viscosity of about 1200 to 1500 centistokes at 25° C. Such a fluid is available as SF1066® organosilicone surfactant (sold by General Electric Company). Polysiloxane ethylene glycol ether copolymers are preferred copolymers for use in the present compositions.

Non-volatile hydrocarbon oils useful in the deodorant compositions of the present invention include straight chain mineral oils and certain branched-chain hydrocarbons. Examples of these fluids are disclosed in U.S. Pat. No. 5,019,375 issued to Tanner et al. on May 28, 1991, incorporated by reference herein.

Preferred mineral oils have the following properties:

(1) viscosity from about 5 centistokes to about 70 centistokes at 40° C.;

(2) density between about 0.82 and 0.89 g/cm$^3$ at 25° C.;

(3) flash point between about 138° C. and about 216° C.; and (4) carbon chain length between about 14 and about 40 carbon atoms.

Particularly preferred straight chain mineral oils include Norpar 15®, which contains between about 14 and about 18 carbon atoms.

Preferred branched chain hydrocarbon oils have the following properties:

(1) density between about 0.79 and about 0.89 g/cm$^3$ at 20° C.

(2) boiling point greater than about 250° C.; and (3) flash point between about 110° C. and about 200° C.

Particularly preferred branched-chain hydrocarbons include Permethyl 103A®, which contains an average of about 24 carbon atoms; Permethyl 104A®, which contains an average of about 68 carbon atoms; Permethyl 102A®, which contains an average of about 20 carbon atoms; all of which may be purchased from Permethyl Corporation; and Ethylflo 364®, which contains a mixture of 30 carbon atoms and 40 carbon atoms and may be purchased from Albermarle Corp.

Intermediate polarity co-solvent emollients are also useful in the cosmetic stick composition of the present invention. In addition to providing cosmetic feel benefits, these emollients also reduce the visible product residue upon application, by increasing the solubility of at least one of the solidifying agents. Co-solvent emollients useful in the present invention have solubility parameters between about 5 and about 12. Solubility parameters are common to the art of cosmetic stick formulation and the means to determine them are disclosed by C. D. Vaughan, "Solubility Effects in Product, Package, Penetration and Preservation" 103 Cosmetics and Toiletries 47–69, October, 1988; and C. D. Vaughan, "Using Solubility Parameters in Cosmetics Formulation", 36 J Soc. Cosmetic Chemists 319–333, September/October, 1985. In the case where the co-solvent emollient has an associated HLB, the HLB value should be less than about 10.

Co-solvent emollients useful in the present invention can be selected from the group consisting of polyoxyethylene; polyoxypropylene; and co-polymers of polyoxyethylene with polyoxypropylene; ethers of fatty alcohols having from about 2 to about 22 carbon atoms; esters of monobasic carboxylic acids having from about 2 to about 22 carbon atoms with alcohols having from about 2 to about 22 carbon atoms; esters of dibasic carboxylic acids having from about 2 to about 12 carbon atoms with alcohols having from about 2 to about 22 carbon atoms; esters of monobasic carboxylic acids having from about 2 to about 22 carbon atoms with polyhydric alcohols having from about 2 to about 12 carbon atoms; esters of dibasic carboxylic acids having from about 2 to about 12 carbon atoms with polyhydric alcohols having from about 2 to about 12 carbon atoms; ethoxylated, propoxylated, and mixtures of ethoxylated and propoxylated ethers of fatty alcohols having from about 2 to about 22 carbon atoms and a degree of ethoxylation and/or propoxylation of below about 50; ethoxylated, propoxylated, and mixtures of ethoxylated and propoxylated esters of monobasic carboxylic acids having from about 2 to about 22 carbon atoms and a degree of ethoxylation and/or propoxylation of below about 50; ethoxylated, propoxylated, and mixtures of ethoxylated and propoxylated esters of dibasic carboxylic acids having from about 2 to about 12 carbon atoms and a degree of ethoxylation and/or propoxylation of below about 50; triglycerides, diglycerides and monoglycerides of monobasic carboxylic acids having from about 2 to about 22 carbon atoms; and mixtures thereof. All of the hydrocarbon functional groups of the carboxylic acids and fatty alcohols referenced above include aliphatic straight-chain, aliphatic branched-chain and aromatic groups and mixtures thereof.

Preferred is the group comprising propoxylated ethers of $C_4$–$C_{18}$ fatty alcohols having a degree of propoxylation below about 50 (e.g. PPG-3-myristyl ether, PPG-14-butyl ether); esters of $C_2$–$C_8$ alcohols with $C_8$–$C_{22}$ carboxylic acids (e.g. ethyl myristate, isopropyl palmitate); esters of $C_{12}$–$C_{15}$ alcohols with benzoic acid (e.g. Finsolv® TN supplied by Finetex); diesters of $C_2$–$C_8$ alcohols with adipic, sebacic, and phthalic acids (e.g., diisopropyl sebacate, diisopropyl adipate, di-n-butyl phthalate); polyhydric alcohol esters of $C_6$–$C_{22}$ carboxylic acids (e.g., propylene glycol dicaprate/dicaprylate, propylene glycol isostearate, PEG-6 caprylic/capric glycerides); and mixtures thereof.

C. High HLB Solubilizing Agent

A surfactant material or mixture of surfactant materials, herein defined as the solubilizing agent, with a high hydrophile-lipophile balance (HLB) is incorporated in the current invention to facilitate dissolution of the particulate deodorant active material out from the fatty product layer after application to the skin. The HLB is a measure of the balance of the size and strength of the hydrophilic and lipophilic groups of a surfactant compound. See "The HLB SYSTEM, a Time Saving Guide to Emulsifier Selection", ICI Americas, Inc., Wilmington, Del., 1980, hereby incorporated by reference.

As the emollients and the solidifying agents useful in the deodorant compositions of the present invention tend to be of low to intermediate polarity, dissolution of the active ingredient, typically a water-soluble material, requires the addition of the high HLB solubilizing agent. A surfactant material or mixture of surfactant materials are useful as the solubilizing agent in the current invention. The solubilizing agent typically has an HLB value greater than about 10 and preferably greater than about 12. The high HLB solubilizing agent is typically incorporated in the deodorant cosmetic stick compositions of the present invention at levels from about 0.05% to about 10%, preferably 0.2% to about 5% and more preferably from about 0.5% to about 3% by weight of the cosmetic stick composition.

Typical solubilizing agents are selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; and polyoxyethylene glyceryl diesters having the formula $R_1COOCH_2CH(OOCR_2)CH_2(OCH_2CH_2)_nOH$—preferably, the polyoxyethylene ethers—wherein: $R_1$ and $R_2$ are the same or different alkyl, alkenyl, or aromatic hydrocarbon radical which may be substituted or unsubstituted—preferably an alkyl radical—having from about 2 to about 22 carbon atoms; and n is from about 2 to about 200.

Preferred examples of such solubilizing agents include: ceteth-8 through ceteth-30, steareth-8 through steareth-30, ceteareth-8 through ceteareth-30, PEG-8 stearate through PEG-30 stearate, PEG-12 isostearate, PEG-40 hydrogenated castor oil, and PEG-20 glyceryl stearate; more preferably, ceteareth-20, steareth-20, and PEG-20 stearate; and most preferably, ceteareth-20.

D. Optional Ingredients

The cosmetic stick deodorant compositions of the present invention may also contain optional components which act as additional active ingredients or which modify the physical characteristics of the composition or the components making up said compositions. Such components are well known in the art. A non-limiting group of these optional components include colorants, perfumes, thickeners (discussed in detail as follows), distributing agents, emulsifiers, bacteriostats, fungistats, and mixtures thereof. Optional components useful herein are described in the following references: U.S. Pat. No. 4,049,792 issued to Elsnau on Sep. 20, 1977; Canadian Patent 1,164,347 which issued to Beckmeyer et al. on Mar. 27, 1984; European Patent Application 117,070 which published on Aug. 29, 1984; and Geria, "Formulation of Stick Antiperspirants and Deodorants", *Cosmetics and Toiletries*, 99:55–60 (1984), all of which are hereby incorporated by reference.

Thickeners can be useful in the deodorant compositions of the present invention. Their selection and the level at which they are used at should be so as not to significantly affect the aesthetics of the solid deodorant composition. Typically, thickeners are used at levels of less than about 5%, preferably less than about 3% and more preferably from about 0.5% to about 3%. Examples of said thickeners are disclosed in U.S. Pat. No. 4,985,238, Tanner et al., issued Jan. 15, 1991; herein incorporated by reference. These thickeners include particulate and filler materials. Such materials are disclosed in U.S. Pat. No. 5,019,375, Tanner et al., issued May 28, 1991, hereby incorporated by reference. Suitable filler materials include colloidal fumed silica (such as Cab-O-Sil®, sold by Cabot Corp.), clays (such as bentonite), hydrophobic (quaternized) clays, silica/alumina thickeners, silicate powders such as talc, alumina silicate, and magnesium silicate, modified corn starches, and mixtures thereof. The use of such fillers as stabilizing agents in cosmetic sticks is disclosed in U.S. Pat. No. 4,126,679, Davy et al., issued Nov. 21, 1987, incorporated by reference. Examples of other particulate materials include particulate hydrophilic polymers such as cellulose ether polymers, modified starches, polyamides, and polypeptides.

METHODS FOR USE

The present invention provides methods for preventing malodor associated with human perspiration. These methods comprise applying to the skin of a human, particularly the skin of the underarm, a safe and effective amount of the deodorant cosmetic stick of the present invention. The term "a safe and effective amount" as used herein, is an amount which is effective in eliminating or reducing malodor associated with human perspiration while being safe for human use at a reasonable risk/benefit ratio. Typically, the safe and effective amount used is from about 0.1 gram per axilla to about 1.5 grams per axilla.

METHODS OF MANUFACTURE

The cosmetic stick deodorant compositions of the present invention may be produced using methods known in the art. Such processes typically comprise the steps of:

(a) admixing the essential and optional composition materials at a temperature sufficient to melt the waxes and dissolve them in the liquid ingredients of the composition;

(b) pouring the composition into stick-form molds, and (c) cooling to form a solid stick composition.

Typically, the wax materials and emollient materials are admixed at a temperature of from about 70° C. to about 95° C., depending upon the type and level of waxes and other composition components. The active ingredient, surfactant and optional ingredients are then added. The bulk composition is typically cooled to a temperature of from about 45° C. to about 60° C. prior to pouring into stick-form molds. Care should be taken in the processes of making these compositions so as to maintain uniform distribution of particulate materials throughout the stick deodorant. Specific essential and non-essential materials to be included, and their levels, are selected in order to produce a stick of desired hardness, so as to maintain dimensional stability while depositing a suitable amount of deodorant active on the skin during normal use.

It has been found that, in the processes for making stick deodorants described above, if the temperature of the composition is carefully controlled prior to pouring the composition into stick-form molds, then preferred compositions of this invention may be produced. In preferred processes for making the stick deodorants of this invention, the compositions are cooled immediately prior to step (c) of the process described above, to a temperature at or slightly above the temperature at which the stick composition begins to solidify, but sufficiently high so as to allow pouring of the composition into stick-form molds. The preferred pouring temperature may vary according to the particular composition employed and can be easily determined experimentally.

EXAMPLES

The following examples further describe and demonstrate embodiments within the scope of the present invention. These examples are solely for the purpose of illustration and are not to be construed as limitations of the present invention as many variations are possible without departing from the spirit or scope thereof.

The levels of the components in the examples below are expressed by total weight of the composition.

| Component | I | II | III | IV |
|---|---|---|---|---|
| Cyclomethicone D-5[1] | 48.47 | 56.10 | 49.47 | 43.97 |
| Stearyl alcohol | 18.50 | 18.50 | 20.00 | 20.50 |
| PPG-14-Butyl Ether[2] | 10.00 | 5.00 | 5.00 | 5.00 |
| Hydrocarbon Oil[3] | — | — | 5.00 | 6.00 |
| Aluminum Zirconium Trichlorohydrex Glycinate[4] | 5.00 | 5.00 | — | — |
| Aluminum Chlorohydroxide | — | — | 5.00 | 9.00 |
| C12–15 Alcohols Benzoate[5] | 5.00 | 2.50 | — | — |
| Castor Wax | 5.00 | — | 5.50 | 5.50 |
| Ozokorite Wax | — | 5.00 | — | — |
| Talc | — | — | 4.00 | 4.00 |
| Perfume | 3.40 | 3.40 | 3.40 | 3.40 |
| Dimethicone[6] | 2.00 | 2.00 | 2.00 | 2.00 |
| PPG-3-Myristyl Ether | 1.50 | 1.50 | — | — |
| Ceteareth-20 | 0.50 | 0.50 | 0.50 | 0.50 |
| Fumed Silica[7] | 0.50 | 0.50 | — | — |
| Behenyl Alcohol | 0.13 | — | 0.13 | 0.13 |
| | 100.00 | 100.00 | 100.00 | 100.00 |

[1]Dow Corning 245 Fluid-cycle polydimethylsiloxane
[2]Fluid AP Supplied by Union Carbide Co.
[3]Norpar 15 Supplied by Exxon Chemical Co.
[4]Supplied by Westwood Chemical Co.
[5]Finsolv TN supplied by Finetex Co.
[6]SF 1075 methyl-phenyl fluid supplied by General Electric Corp.
[7]Cab-O-Sil supplied by Cabot Corp.

The deodorant cosmetic sticks compositions of the present invention are prepared by combining all of the ingredients of the composition and heating to from about 70° C. to about 95° C. to form a clear homogeneous solution. The solution is then cooled to a mixing temperature of from about 45° C. to about 60° C. The mixture is then poured into stick-form molds. Upon cooling a stable deodorant stick is obtained.

Although particular examples of deodorant cosmetic stick compositions of the present invention have been described, modifications may be made without departing from the spirit and scope of the present invention. Accordingly, the present invention comprises all embodiments within the scope of the claims.

All percentages herein are by weight of the total composition and all ratios are weight ratios unless otherwise indicated. All percentages, ratios and levels of ingredients referred to herein are based upon the actual amount of the ingredient, and do not include solvents, fillers, or other materials with which the ingredient may be combined when supplied commercially, unless otherwise indicated.

All numerical ranges specified herein, hereby expressly include each and every numerical value therebetween, as if it were expressly written therein.

We claim:

1. A cosmetic stick deodorant composition comprising:
   a. from about 0.5% to about 10.0% of the cosmetic stick deodorant composition of an astringent metal salt active;
   b. a stable, anhydrous base component comprising:
      i. from about 5% to about 40% of the cosmetic stick deodorant composition of a solidifying agent selected from the group consisting of the high melting point waxes; and low melting point wax fatty alcohols, fatty acid esters and fatty acid amides, having fatty chains of from about 8 to about 22 carbon atoms, and mixtures thereof;
      ii. from about 20% to about 70% of the cosmetic stick deodorant composition of a volatile emollients;
      iii. from about 10% to about 50% of the cosmetic stick deodorant composition of non-volatile emollients; and
   c. from about 0.05% to about 10% of the cosmetic stick deodorant composition of a solubilizing agent having a hydrophile-lipophile balance (HLB) value of greater than about 10.

2. A cosmetic stick deodorant composition according to claim 1, wherein the astringent metal salt active is selected from the group consisting of aluminum halides, aluminum hydroxy-halides, zirconyl oxyhalides, zirconyl hydroxy-halides, zinc compounds, complexes of aluminum, zirconium and amino acids, and mixtures thereof.

3. A cosmetic stick deodorant composition according to claim 2, wherein the solidifying agent of the base component is selected from the group consisting of castor wax, ceresin wax, ozokerite wax, white beeswax, synthetic waxes, cetyl alcohol, palmitic acid, stearyl alcohol, behenyl alcohol, sucrose esters of tallow fatty acids, mono and di-fatty acid ester of polyethylene glycol, and mixtures thereof.

4. A cosmetic stick deodorant composition according to claim 3, wherein the volatile emollients of the base component are selected from the group consisting of: cyclic volatile silicone oils corresponding to the formula:

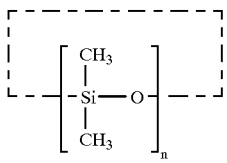

wherein n is from about 3 to about 7; linear volatile silicones corresponding to the formula:

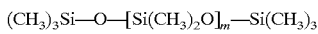

wherein m is from about 1 to about 7; volatile hydrocarbon oils and mixtures thereof.

5. A cosmetic stick deodorant composition according to claim 4, wherein the non-volatile emollients are selected from the group consisting of non-volatile silicone oils including polyalkylsiloxanes, polyarylsiloxanes, polyalkylarylsiloxanes, and poly-ethersiloxane copolymers; non-volatile hydrocarbon oils, and mixtures thereof.

6. A cosmetic stick deodorant composition according to claim 5, wherein the solubilizing agent material having a hydrophile-lipophile balance (HLB) value of greater than 10 is selected from the group consisting of polyoxyethylene ethers having the formula $R_1(OCH_2CH_2)_nOH$; polyoxyethylene esters having the formula $R_1CO(OCH_2CH_2)_nOH$; polyoxyethylene glyceryl esters having the formula $(R_1COO)CH_2CH(OH)CH_2(OCH_2CH_2)_nOH$ or having the formula $HOCH_2CH(OOCR_1)CH_2(OCH_2CH_2)_nOH$; polyoxyethylene glyceryl diesters having the formula $R_1COOCH_2CH(OOCR_2)CH_2(OCH_2CH_2)_nOH$, wherein: $R_1$ and $R_2$ are the same or different alkyl, alkenyl, or aromatic hydrocarbon radical which may be substituted or unsubstituted, having from about 2 to about 22 carbon atoms; and n is from about 2 to about 80 and mixtures thereof.

7. A cosmetic stick deodorant composition comprising:
   a. from about 4% to about 5% of the cosmetic stick deodorant composition of an astringent metal salt deodorant active and;
   b. a stable, anhydrous base component comprising:
      i. from about 15% to about 30% of the cosmetic stick deodorant composition of a solidifying agent;
      ii. from about 40% to about 60% of the cosmetic stick deodorant composition of volatile emollients
      iii. from about 15% to about 25% of the cosmetic stick deodorant composition of non-volatile emollients and;
   c from about 0.5% to about 3% of the cosmetic stick deodorant composition of a solubilizing agent material having an HLB value of greater than about 12.

8. A cosmetic stick deodorant composition according to claim 7 wherein the astringent metal salt active is selected from the group consisting of aluminum chlorohydroxide or aluminum zirconium trichlorohydrex glycinate complex and mixtures thereof.

9. A cosmetic stick deodorant composition according to claim 8 wherein the solidifying agent of the base component is selected from the group consisting of castor wax, stearyl alcohol, behenyl alcohol and mixtures thereof.

10. A cosmetic stick deodorant composition according to claim 9 wherein the volatile emollients of the base component, comprises the cyclic volatile silicone corresponding to the formula:

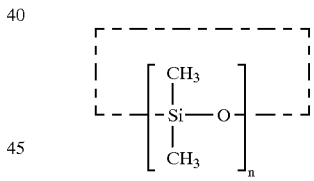

wherein n is equal to about 5.

11. A cosmetic stick deodorant composition according to claim 10 wherein the non-volatile emollients are selected from the group consisting of: dimethicone having a viscosity of from about 15 to about 65 cp., the hydrocarbon oil Norpar 15®, PPG- 14-butyl ether or PPG-3-myristyl ether, esters of C12–15 alcohol with benzoic acid, and mixtures thereof.

12. A cosmetic stick deodorant composition according to claim 11 wherein the solubilizing agent having an HLB value greater than 12 is ceteareth-20.

13. A cosmetic stick deodorant composition according to claim 12 which additionally comprises from about 0.5% to about 3% of colloidal fumed silica as a thickener.

14. A method for preventing malodor associated with human perspiration by administering a safe and effective amount of the composition of claim 1 to a human in need of such treatment.

* * * * *